United States Patent [19]
Onoda

[11] Patent Number: 5,284,151
[45] Date of Patent: Feb. 8, 1994

[54] ELECTROCARDIOGRAPH SYSTEM

[75] Inventor: Masahiro Onoda, Kanagawa, Japan

[73] Assignee: Terumo Kabushiki Kaisha, Tokyo, Japan

[21] Appl. No.: 800,139

[22] Filed: Nov. 29, 1991

[30] Foreign Application Priority Data

Nov. 30, 1990 [JP] Japan .................. 2-330253

[51] Int. Cl.⁵ .......................... A61B 5/0432
[52] U.S. Cl. ................... 128/710; 128/908
[58] Field of Search ............... 128/696, 210, 711, 901,
128/902, 908; 364/413.06; 346/33 ME, 33 B, 870.31

[56] References Cited

U.S. PATENT DOCUMENTS

| | | | |
|---|---|---|---|
| 3,587,564 | 6/1971 | Hagan et al. | 128/711 |
| 3,867,950 | 2/1975 | Fischell | 128/419 PS |
| 3,937,214 | 2/1976 | Hutchins, IV | 128/908 |
| 4,006,748 | 2/1977 | Schulman | 128/419 P |
| 4,109,644 | 8/1978 | Kojima . | |
| 4,243,044 | 1/1981 | Blancke | 128/696 |
| 4,537,200 | 8/1985 | Widrow | 128/696 |
| 4,715,385 | 12/1987 | Cudahy et al. | 128/710 |
| 4,794,532 | 12/1988 | Leckband et al. | 128/710 |
| 4,941,201 | 7/1990 | Davis | 128/419 PT |
| 5,025,808 | 6/1991 | Hafner | 128/710 |

FOREIGN PATENT DOCUMENTS 2315064 of 0000 Fed. Rep. of Germany .
59-212949 of 0000 Japan .
2-295545 of 0000 Japan .

OTHER PUBLICATIONS

European Search Report, 91120598.7 Printed Publication "R.F. Powered Cage System for Implant Biotelemetry", IEEE.
Transactions of Biomedical Engineering, vol. BME. 27, No. 8, pp. 460-467, Ko et al., Aug. 1980.

Primary Examiner—William E. Kamm
Attorney, Agent, or Firm—Burns, Doane, Swecker & Mathis

[57] ABSTRACT

An electrocardiograph system which enables safe data transfer with high reliability between a portable electrocardiograph and a recorder, such as a printer, and in which an effect of leakage magnetism is taken into consideration. In the electrocardiograph system, electrical signals and/or electric power are transferred between the electrocardiograph and the recorder by electromagnetic coupling therebetween using independent coils. The electrocardiograph system is further provided with a device for rejecting noise of an electric power signal from the electrical signals or noise of an electrical power signal and a clock signal from a data signal.

7 Claims, 9 Drawing Sheets

ELECTROCARDIOGRAPH SYSTEM

BACKGROUND OF THE INVENTION

1. Field of the Invention

The present invention relates to an electrocardiograph system comprising an electrocardiograph recorder and a printer, and particularly to a data transfer system between a small portable electrocardiograph recorder and an electrocardiogram printer.

2. Description of the Related Art

In conventional portable (holder) electrocardiographs, after an electrocardiogram is magnetically recorded on an electrocardiogram recording medium for 24 hours using a magnetic tape, the electrocardiogram is analyzed by a private analysis apparatus while being reproduced thereby, and the analytical results are printed. Such an electrocardiograph system has the faults that analysis and printing require much time and that a magnetic recording/reproducing system causes distortion in the waveform measured. The electrocardiograph system also has the problems that since analysis is performed by high-speed reproduction,-analysis cannot be performed for a sufficient time with high accuracy, and that the apparatus used is limited in reduction in its size and is expensive.

In addition, an electrocardiograph system has recently been developed in which the body of a portable electrocardiograph recorder contains a solid-state (semiconductor) memory and a microcomputer so that the electrocardiogram is analyzed in real time by the microcomputer during measurement for 24 hours, and the analytical results and the electrocardiogram waveform are recorded on the solid-state (semiconductor) memory. Such a system comprising a portable electrocardiograph recorder having a body which contains a memory generally employs a data transfer method in which a connector attached to the body of a portable electrocardiograph recorder is electrically connected to a connector attached to the printer and having electrical contact points when the electrocardiogram data recorded on the memory is output to a printer. However, this system has the problems that an increase in number of connections causes deterioration in the reliability because the connector has a mechanical portion, and that since there is an electrical connection, a human body is in danger if being connected to the body of the portable electrocardiograph recorder.

On the other hand, JPA 59-212949 (laid open to public on Dec. 1, 1984; corresponding U.S. Pat. No. 4,720,636) discloses electro-magnetic couplings for transferring electric power, clock and data between an IC card and a card processor. In JPA 59-212949, the electric power and clock are transferred by a common contact point, and the data is transferred by two contact points which are independently provided in the transmitting and receiving directions.

However, although the common use of the contact point for the electric power and clock causes no danger of mixing noises having different frequencies because the transfer frequency of the electric power is the same as that of the clock, the common use produces an unstable factor during receiving of the clock because the magnetic signal is distorted by a variation in the load. Further, since the area and the number of turns of a coil is increased in order to connect magnetically and efficiently more electric power, the inductance of coil is increased and it results in that the self-induction voltage is increased and that the current flowing through coil is reduced as the transfer frequency is high. Therefore, the common use of the contact point for the electric power and clock limits the setection of the transfer frequency of clock.

SUMMARY OF THE INVENTION

It is an object of the present invention to provide an electrocardiograph system which has none of the problems of conventional systems and which enables safe data transfer with high reliability between an electrocardiograph recorder and a printer.

In order to achieve the object, an electrocardiograph system of the present invention comprises an electrocardiograph recorder for measuring an electrocardiogram waveform of a subject and storing the waveform therein, and a recorder for reading and outputting the electrocardiogram waveform stored in the electrocardiograph recorder, wherein the transfer of electrical signals between the electrocardiograph recorder and the printer is achieved by electro-magnetic couplings.

A electric power source is also magnetically connected in the system.

In this system, the electrical signals and the electric power generated from the power source are transferred by electro-magnetic couplings through different contact points, and the electrical signals include clock and data signals. The clock and data signals are transferred by electro-magnetic coupling through different contact points, and the data signal is transmitted and received using a common contact point.

In this system, the electro-magnetic coupling between the electrocardiograph recorder and the printer has no mechanical joint and thus has semipermanent durability. In addition, since there is no electrical connection, this system maintains electrical isolation and is thus safe even if the electrocardiograph recorder is connected to the printer while being connected to a human body.

Further, it is possible to independently set a transfer frequency and select the size and number of turns of a coil which are optimum for each of the electric power and the electrical signals (particular, the clock) and which have high efficiency, and to prevent the instability in the clock, which is caused by a variation of the load. Because of the separation between the electric power and the clock.

In the above-described configuration, when the transfer frequencies of the electric power and the electrical signals (clock, data) are independently selected, since the transfer noise of the electric power dependent on the frequency is mixed in the clock transfer coil and the data transfer coil, some measurement against noise is required. Particularly, during the data transfer from the electrocardiograph recorder to the printer, since the electric power of the electrocardiograph recorder is magnetically supplied from the side of the printer, the electric power is small and is significantly affected by leakage magnetism because the clock coil and the power coil are put in the transmitting state near the data receiving coil.

It is another object of the present invention to provide an electrocardiograph system in which safe data transfer, with high reliability, between an electrocardiograph recorder and a printer is achieved in consideration of an effect of leakage magnetism.

In order to achieve the object, an electrocardiograph system comprises an electrocardiograph recorder for measuring an electrocardiogram waveform of a subject and storing it therein, and a printer for reading and outputting the electrocardiogram waveform stored in the electrocardiograph recorder, wherein electric power and electrical signals are transferred between the electrocardiograph recorder and the printer by independent electro-magnetic couplings therebetween, and noise removing means is provided for preventing at least power noise from being mixed in the electrical signals.

The electrical signals include clock and data signals, and the noise removing means prevents the power noise and/or clock noise from being mixed in the data signal. The noise removing means detects an noise signal and adds the noise signal with the opposite phase to the data signal in a data receiver of the printer.

The noise removing means includes a metal sheet insulating magnetism which is arranged with surrounding connecting portions of said clock signal, data signal and power signal or at least a connecting a portion of said data signal, to reduce a mixture of leakage magnetism into signals.

The above configuration decreases the power noise or other noise mixed in the electrical signals when the electric power and the electrical signals are transferred by independent electro-magnetic couplings.

The above-described and other objects, configuration and effects of the invention are made apparent from the description below of embodiments with reference to the drawings.

DESCRIPTION OF THE PREFERRED EMBODIMENTS

Embodiments of the present invention are described in detail below with reference to the drawings.

Figure 1:
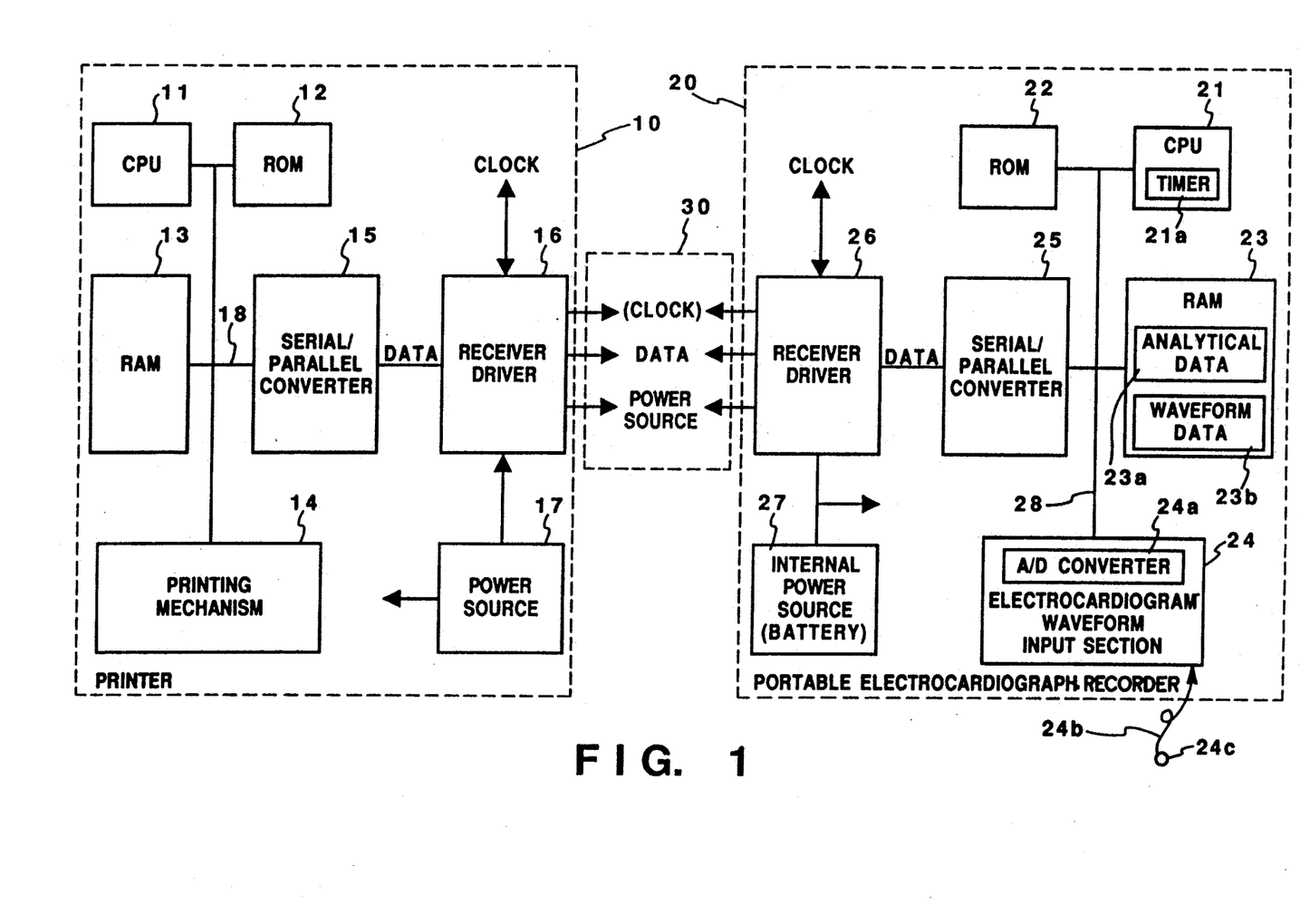
FIG. 1 is a block diagram showing the configuration of an electrocardiograph system in accordance with an embodiment of the present invention.

FIG. 1 is a block diagram showing the configuration of an electrocardiograph system according to an embodiment of the invention.

The system comprises a portable electrocardiograph recorder 20 and a private printer 10 serving as a recorder. The portable electrocardiograph recorder 20 has the size of a cigarette case and is attached to a patient for 24 hours. The electrocardiogram of the patient is analyzed in real time by the microcomputer contained in the body of the portable electrocardiograph recorder 20, and the analytical results and the electrocardiogram waveform are recorded in the solid-state (semiconductor) memory contained in the body. After analysis for 24 hours, the electrocardiogram data recorded in the solid-state (semiconductor) memory is backed up. The private printer 10 reads and outputs the electrocardiogram data recorded in the solid-state (semiconductor) memory of the portable electrocardiogram recorder 20. A conventional portable electrocardiograph system generally uses an electrical connector for connecting a solid-state (semiconductor) memory of the portable electrocardiograph recorder to a private printer when the electrocardiogram data recorded in the memory is read and output to the private printer. However, such an electrical connector has the faults that an increase in number of connections causes deterioration in the reliability of contact points, that it is physically large, and that the electrical connection causes danger when the apparatus is connected to a human body. The system of the embodiment is provided with a electro-magnetic coupler without any electrical connection. Such a electro-magnetic coupler has the characteristics that since there is no electrical contact point, the life of contact points is semipermanent, and that since there is no electrical connection, the connector is safe even when being connected to a human body. The electro-magnetic coupler can be thinned by using sheet-like coils. (Example of Configuration of Electrocardiograph System)

As shown in FIG. 1, the portable electrocardiograph recorder 20 is connected to the private printer 10 by the electro-magnetic coupler 30.

The portable electrocardiograph recorder 20 comprises a CPU 21 for operation and control which has a timer 21a for setting intervals of measurement of the electrocardiogram waveform or a measurement limit time of 24 hours. In the drawing, reference numeral 22 denotes an ROM for storing a control program which is executed by the CPU 21, and reference numeral 23 denotes an auxiliary storage RAM having a region 23a for storing analytical data and a region 23b for storing electrocardiogram waveform data. Reference numeral 24 denotes an electrocardiogram waveform input section to which the signal input from a pole 24c of contact with a human body through a cable 24a and converted into a digital value by an A/D converter 24a is input. Reference numeral 25 denotes a serial/parallel converter for converting parallel data on a bus 28 into serial data and outputting the serial data to a receiver/driver 26 and converting serial data input from the receiver/-driver 26 into parallel data and outputting the parallel data to the bus 28. Reference numeral 27 denotes an internal power source such as a battery with small electric power. The serial data, clock and electric power are transferred to the side of the private printer 10 by the electro-magnetic coupler 30 through the receiver/-driver 26.

In the private printer 10, reference numeral 11 denotes a CPU for operation and control; reference numeral 12, an ROM for storing a control program which is executed by the CPU 11; and reference numeral 13, an auxiliary storage RAM. Reference numeral 14 denotes a printing mechanism for printing and outputting the analytical data or waveform data input from the portable electrocardiograph recorder 20. Reference numeral 15 denotes a serial/parallel converter for converting parallel data on a bus 18 into serial data and outputting the serial data to a receiver/driver 16 and converting the serial data input from the receiver/driver 16 into parallel data and outputting the parallel data to the bus 18. Reference numeral 17 denotes an external commercial power source with large power. The serial data, clock and electric power are transferred to the side of the portable electrocardiograph recorder 20 by the electro-magnetic coupler 30 through the receiver/driver 16.

Example of Configuration of Electro-magnetic Coupler

In the case of clock synchronous type serial data transfer in which the private printer is provided on a host side (the side for supplying a transfer clock), and the portable electrocardiograph recorder is provided on a slave side (the side for receiving the transfer clock), the configuration of a electro-magnetic coupler portion is described below with reference to FIG. 2.

Figure 2:
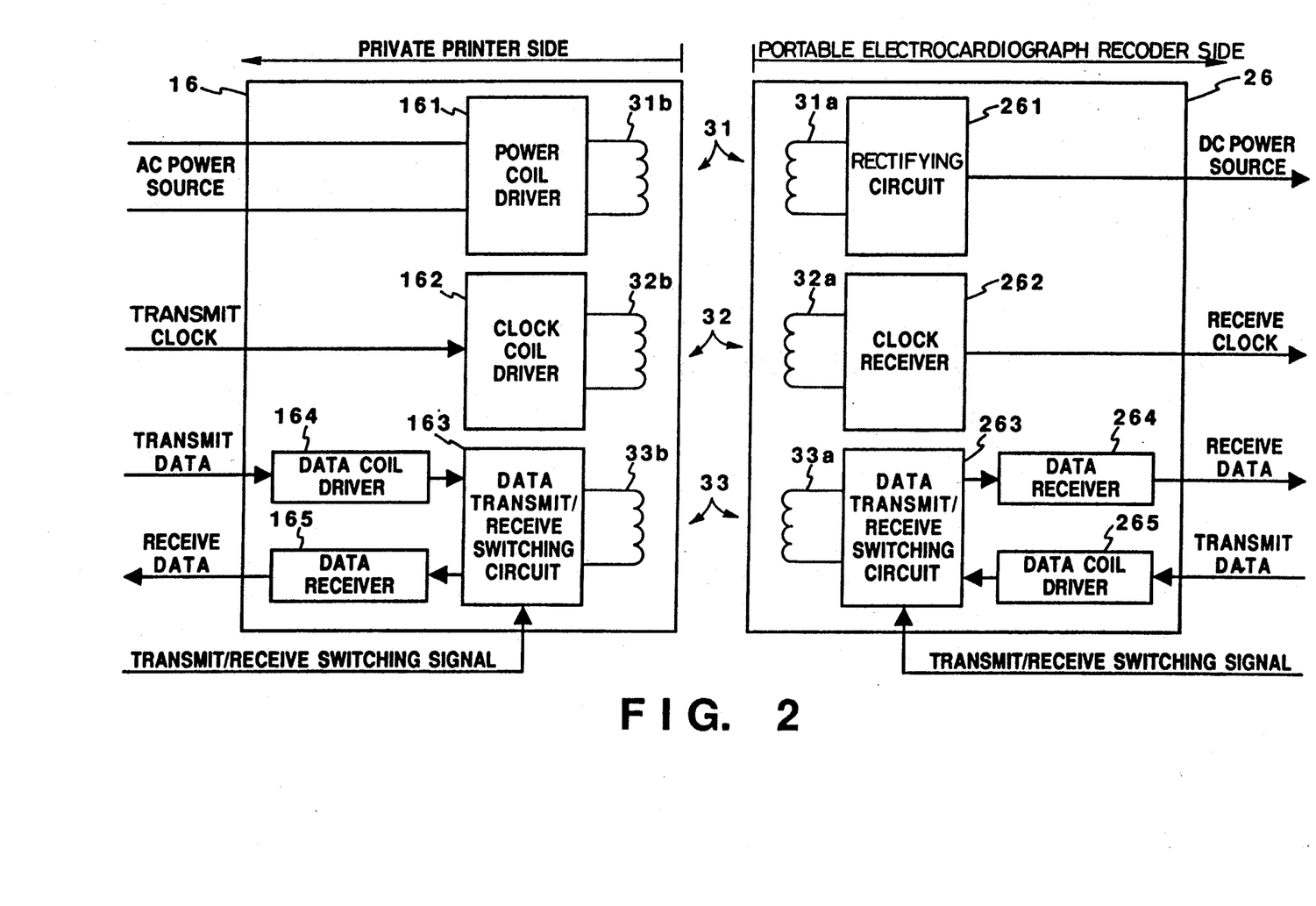
FIG. 2 is a block diagram showing a first embodiment of a electro-magnetic coupling portion.

FIG. 2 is a drawing showing first embodiment of the electro-magnetic coupler portion.

In the electro-magnetic coupler portion, the receiver/driver 16 on the side of the private printer 10 comprises a clock coil driver 162, a clock transfer coil 32b, a data transmit/receive switching circuit 163, a data coil driver 164, a data transfer coil 33b, and a data driver 165 (when electric power is also supplied, further comprising a power coil driver 161 and a power coil 31b ). The receiver/driver 26 on the side of the portable electrocardiograph recorder 20 comprises a clock transfer coil 32a, a clock receiver 262, a data transfer coil 33a, a data transmit/receive switching circuit 263, a data coil driver 265 and a data receiver 264 (when electric power is received, further comprising a power coil 31a and a rectifying circuit 261).

Figure 3:
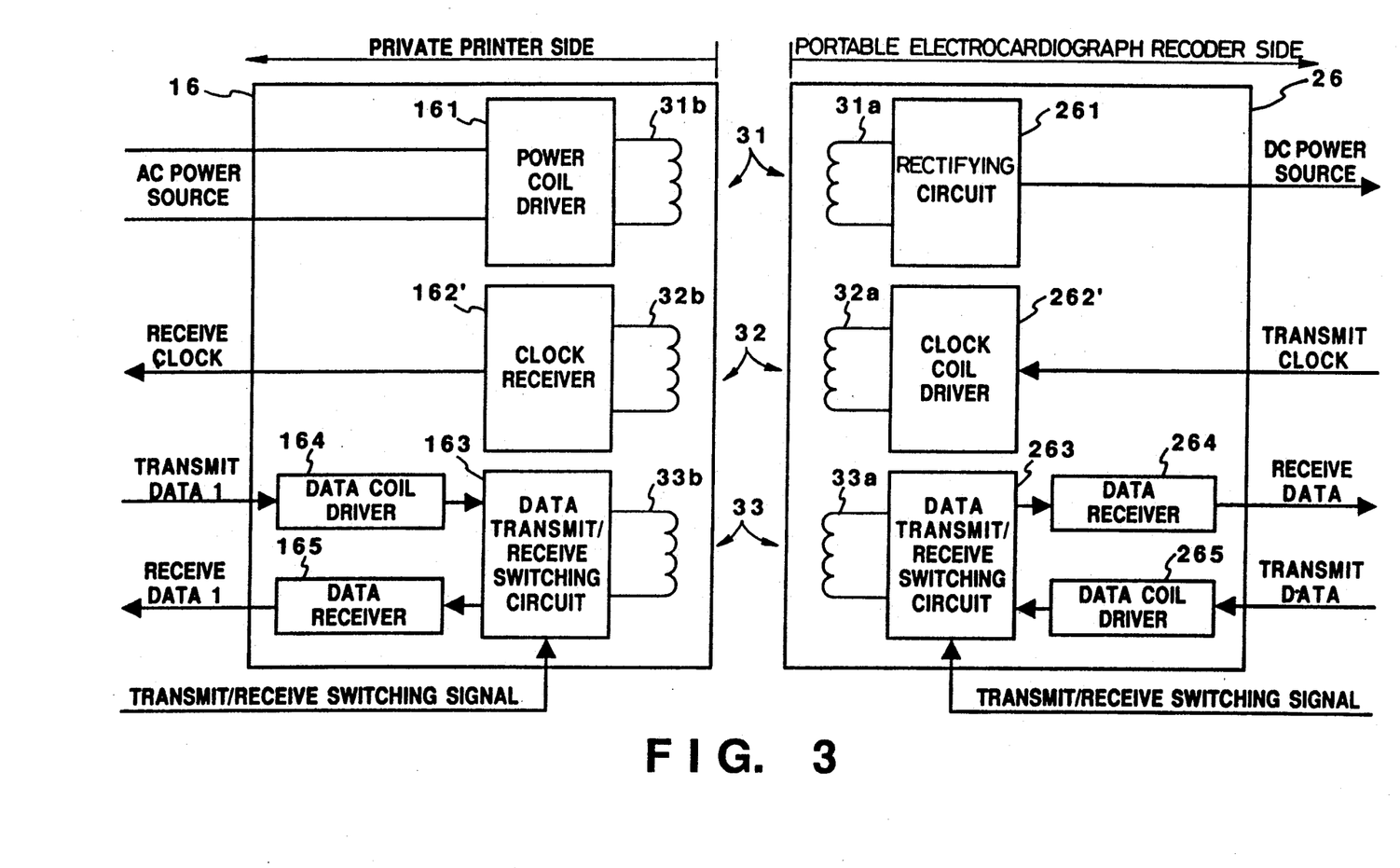
FIG. 3 is a block diagram showing a second embodiment of a electro-magnetic coupling portion.

FIG. 3 is a block diagram showing a second embodiment of the electro-magnetic coupler portion, and shows a possible configuration which has the reversed relation between the host and slave sides. Namely, the portable electrocardiograph recorder supplies the data transfer clock to the private printer. In this embodiment, a clock receiver 162' is provided on the side of the private printer 10, and a clock coil driver 262' is provided on the side of the portable electrocardiograph recorder 20.

Figure 8:
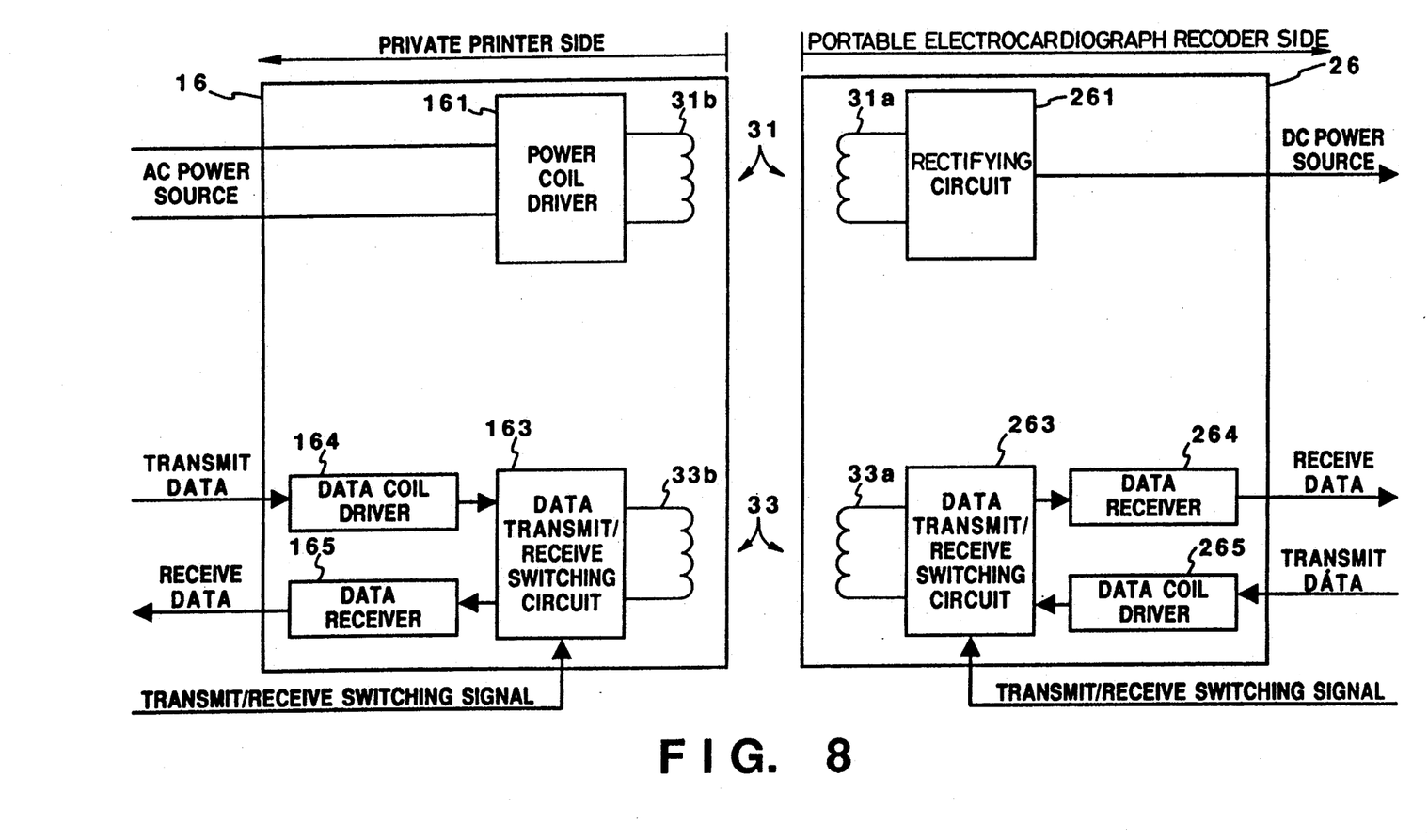
FIG. 8 is a block diagram showing a third embodiment of a electro-magnetic coupling portion.

FIG. 8 shows the configuration of a third embodiment of the electro-magnetic coupler portion.

Figure 9:
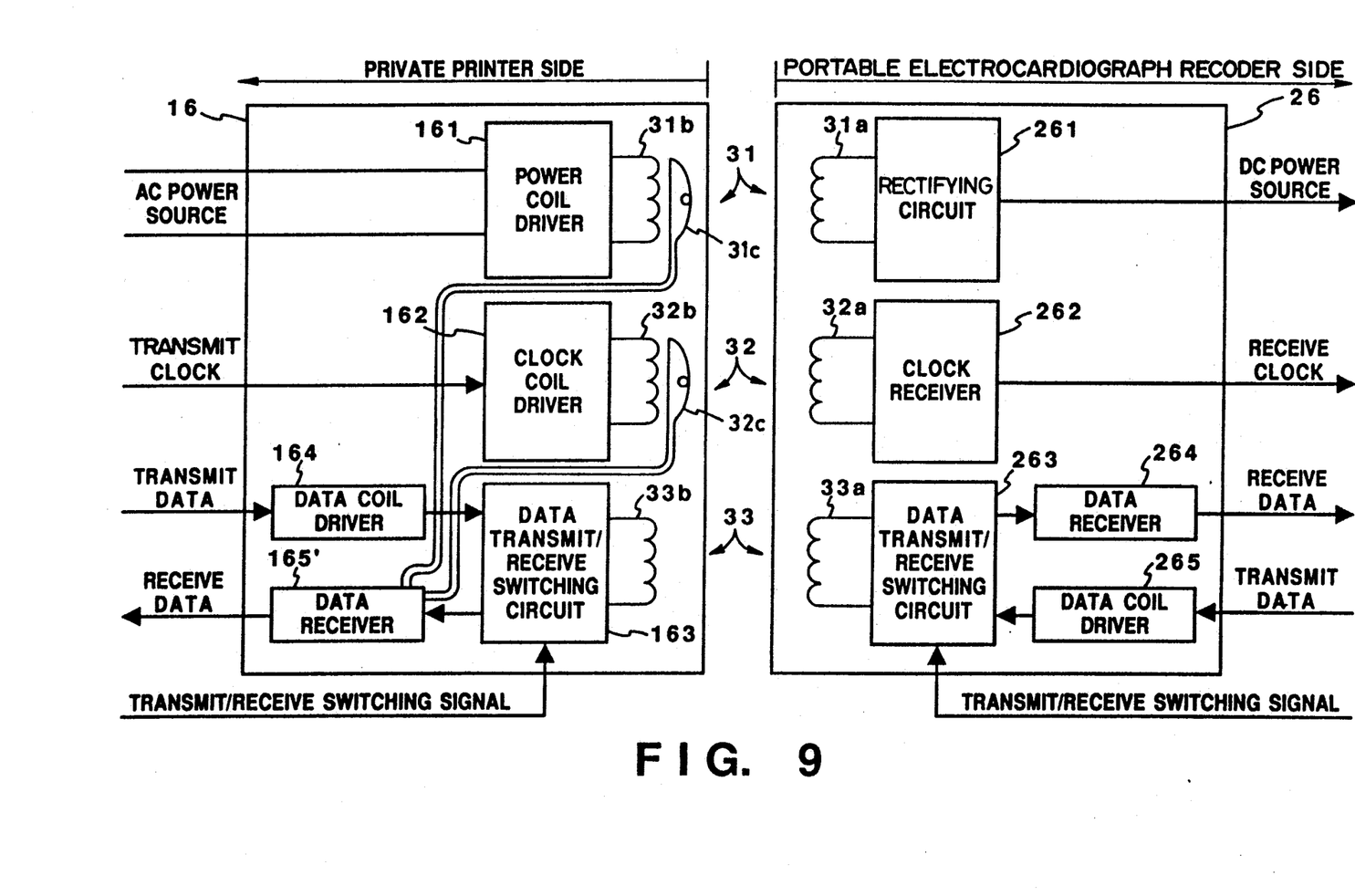
FIG. 9 is a block diagram showing a fourth embodiment of a electro-magnetic coupling portion.

An asynchronous data transfer system enables communication using data only. A configuration in which the clock transmitting/receiving sections are removed from the configuration in the first or second embodiment can be considered as such an asynchronous type. FIG. 9 shows a fourth embodiment of the electro-magnetic coupler for removing noise from coils. In this embodiment, in consideration of the fact that the receiving coil is affected by the power coil and clock coil in the transmission state, particularly, when data is transferred from the electrocardiograph recorder 20 to the printer 10, the noise by the leakage magnetism generated from the power coil and clock coil on the printer side is detected and input to the data receiver 165' of the printer 10 in order to remove or decrease noise.

Figure 10:
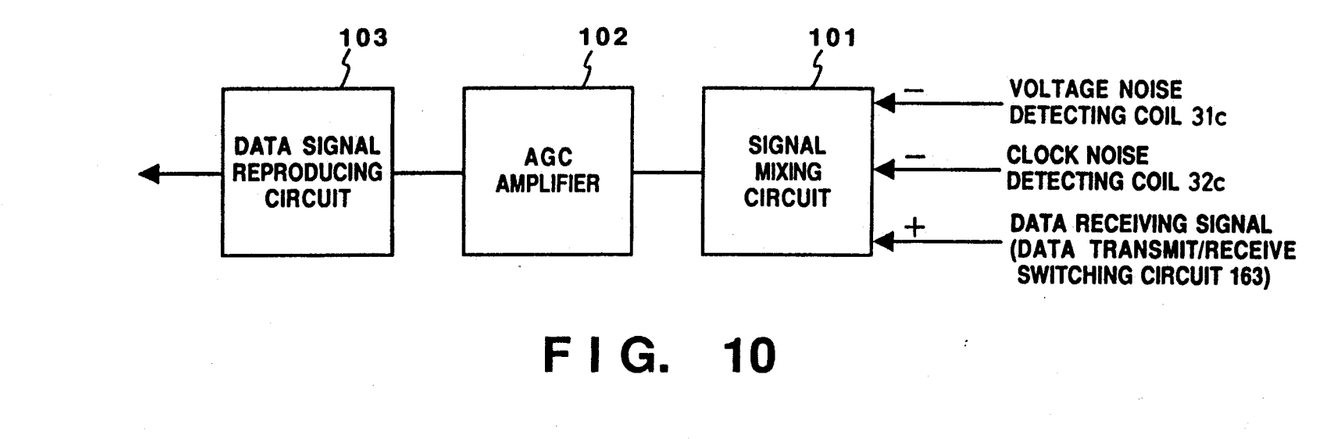
FIG. 10 is a block diagram showing the internal configuration of a data receiver in the fourth embodiment.

FIG. 10 schematically shows an example of the configuration of the data receiver 165' in the fourth embodiment. The noise is detected by detection coils 31c and 32c and added the detected noise from each of the detection coils 31c and 32c with the opposite phase to the data receive signal in order to decrease the noise in a signal mixing circuit 101 of the data receiver 165' shown in FIG. 10. In this configuration, the signal from which noise is removed in the signal mixing circuit 101 is subjected to automatic gain amplification by an AGC amplifier 102 and then converted into serial digital data by a data signal reproducing circuit 103.

Figure 11:
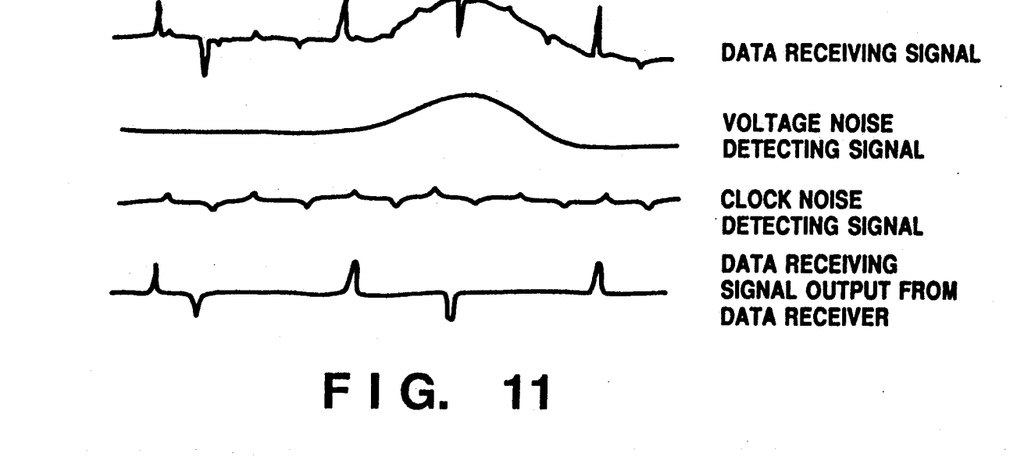
FIG. 11 is a drawing showing noise removal in the data receiver in the fourth embodiment.
Figure 13:
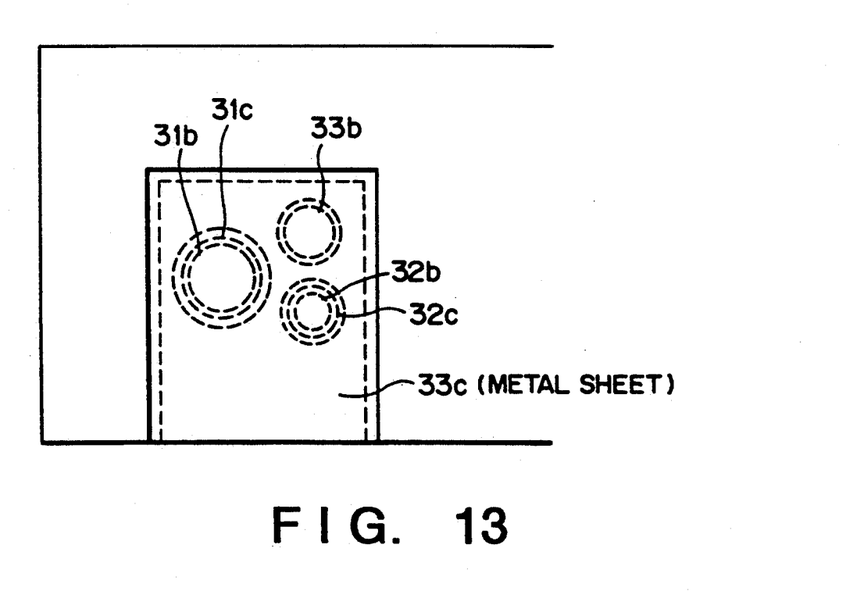
FIG. 13 is a drawing showing the connection of apparatuses in accordance with another embodiment of the present invention.

FIG. 11 is a drawing showing an example of noise removal in the signal mixing circuit 101 shown in FIG. 10. The voltage noise generated from the power coil has a relatively long period, while the clock noise generated from the clock coil has a short period. Additionally, as shown in FIG. 13, by masking a portion other than surface of coil (especialy, the surrounding of the data coil 33b) with the film insulating magnetism, e.g. metal sheet, it becomes possible to reduce the mixture of noise to the data signals.

Examples of Connection of Electro-magnetic Coupler

Figure 4:
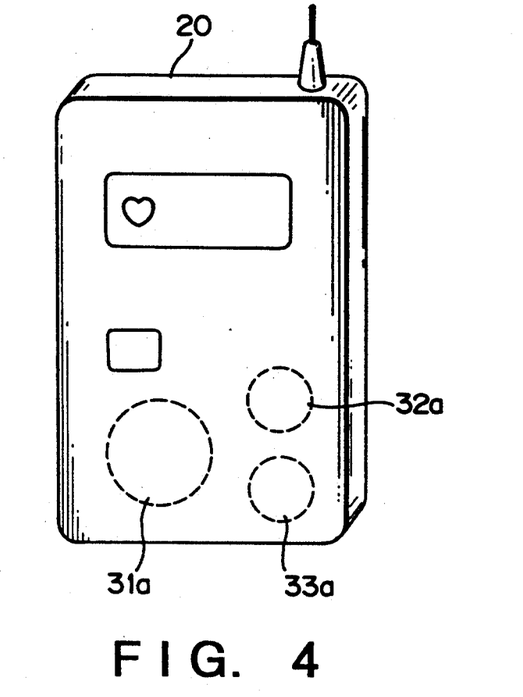
FIGS. 4 to 6 are drawings showing the connection of apparatuses in accordance with an embodiment of the present invention.
Figure 5:
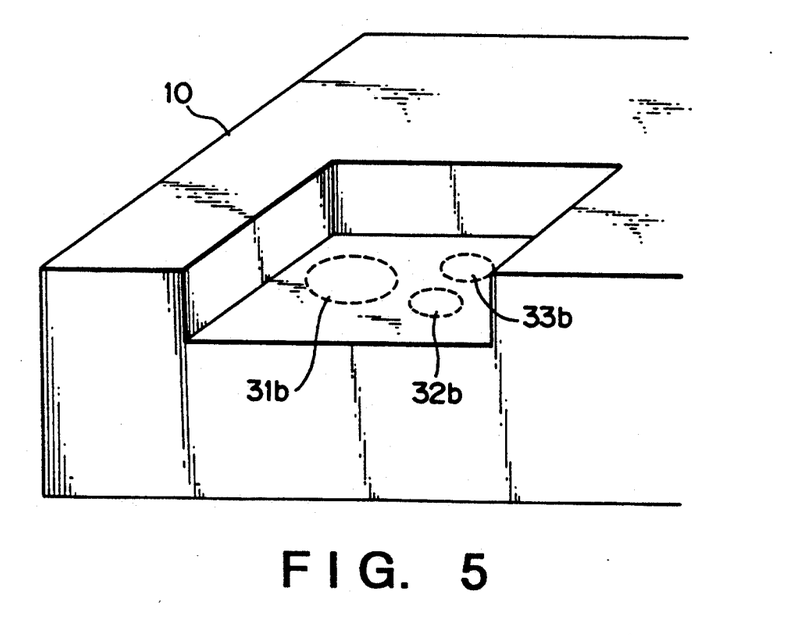
Figure 6:
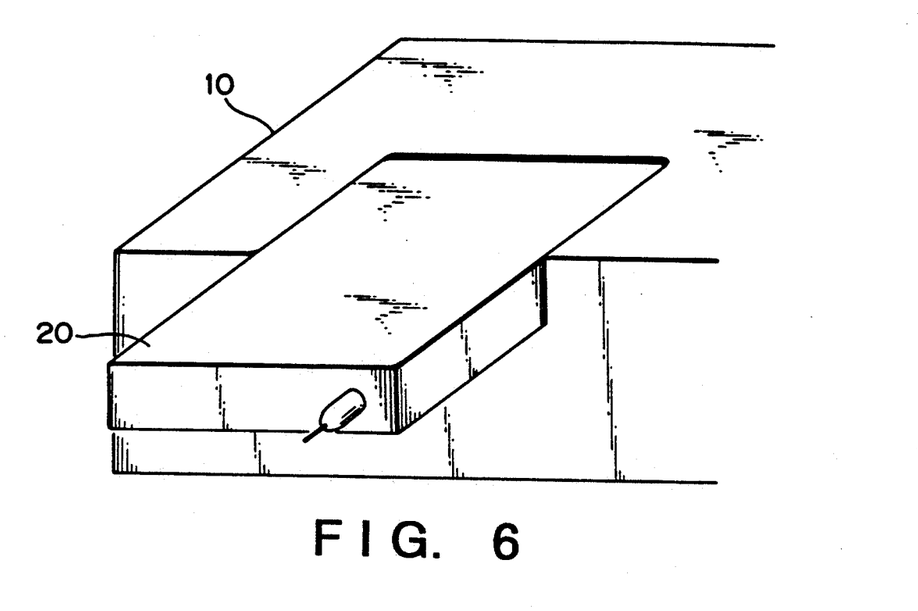
Figure 12:
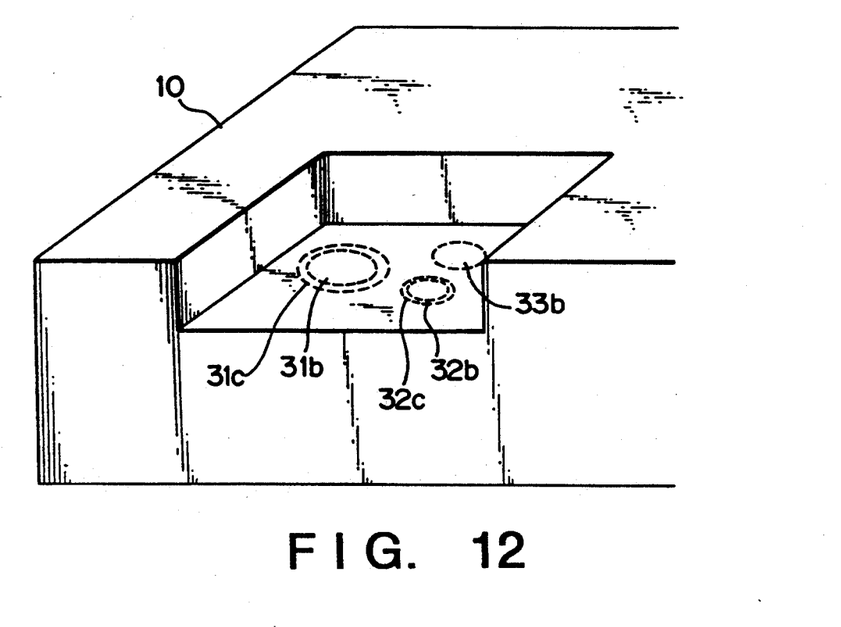
FIG. 12 is a illustration showing an arrangement of coils in a private printer 10 in accordance with a forth embodiment of the present invention.

A clock transfer coil and a data transfer coil (power coil) on the side of the portable electrocardiograph recorder 20 are respectively paired with a clock transfer coil and a data transfer coil (power coil) on the side of the private printer 10. During transfer, the electro-magnetic coupler is connected to both sides by a positioning means, such as the FIG. 5 receptacle of the private printer 10, for positioning the coils so that each of the coil pairs are magnetically connected to each other. Namely, the coupling coils 31a, 32a, 33a of the portable electrocardiograph recorder 20 shown in FIG. 4 are positioned so as to face the coupling coils 31b, 32b, 33b, respectively, of the private printer 10 shown in FIG. 5, thereby connecting the portable electrocardiograph recorder 20 and the private printer 10, as shown in FIG. 6. FIG. 12 shows an arrangement of coils in the private printer 10 in accordance with a forth embodiment of the present invention.

Figure 7:
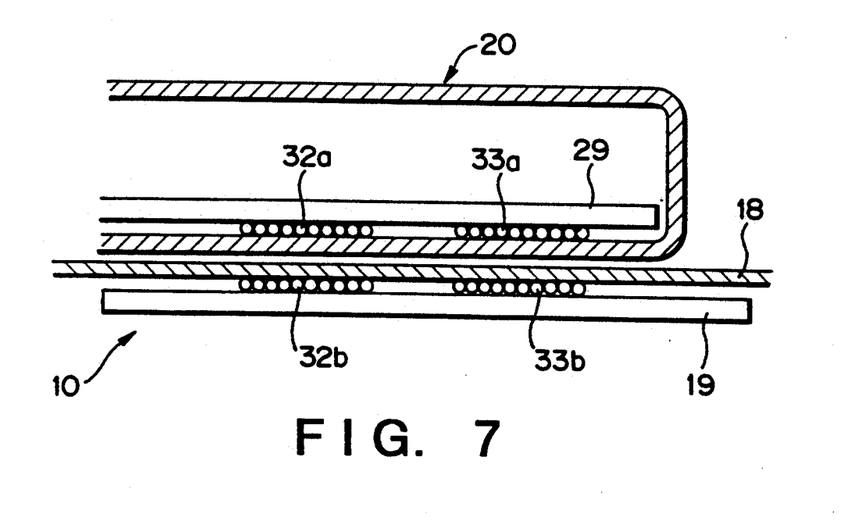
FIG. 7 is a sectional view showing a electro-magnetic coupling portion.

FIG. 7 is a sectional view showing the electro-magnetic coupling portion. Each of the coil pairs 32a, 32b and 33a, 33b are formed on a PC boards 29 and 19, respectively, and electro-mangetically coupled to each other through a casing 28 of the portable electrocardiograph recorder 20 and a casing 18 of the private printer 10. In this way, each of the coils is wound in a plane form.

In a first example of electro-magnetic coupling, during data transfer, the data transfer clock (power) is constantly supplied to the portable electrocardiograph recorder from the private printer 10, and data can be transferred from the portable electrocardiograph recorder 20 to the private printer 10, and vice versa, by operating the data transmit/receive switching circuit of each of the devices. The flow of each of the signals in this case is given below. A portion with an underline shows the flow of a signal on the side of the private printer 10, and a portion without an underline shows the flow of a signal on the portable electrocardiograph recorder 20.

(1) Clock signal clock→clock coil driver→clock transfer coil→[electro-magnetic coupling]→clock transfer coil→clock receiver→receive clock (2) Data signal (During data transfer from the private printer to the portable electrocardiograph recorder)

data→data coil driver→data transmit/receive switching circuit (transmit)→data transfer coil→[electro-magnetic coupling]→data transfer coil→data transmit/receive switching circuit (receive)→data receiver→receive data (During data transfer from the portable electrocardiograph recorder to the private printer)

received data←data receiver←data transmit/receive switching circuit (receive)←data transfer coil←[electro-magnetic coupling]←data transfer coil←data transmit/receive switching circuit (transmit)←data coil driver←data (3) Electric power power coil driver→power coil→[electro-magnetic coupling]→power coil→rectifying circuit→electric power Although the invention is described above with respect to preferred embodiments concerning a portable electrocardiograph system, the invention can provide a connector which has electrical safety and excellent mechanical durability and which is suitable for recording the data recorded once on a recording medium on another medium or printing out the data in another electronic medical apparatus such as an electron clinical thermometer, electron sphygmomanometer or the like.

In addition, the recorder is not limited to the printer, and any apparatuses such as a display, a storage device for simply storing data, a device for reading data of a portable apparatus such as a communication device can be used as recorders.

Various changes, additions and modifications may be made without departing from the spirit and scope of the claims below. The present invention involves such changes, additions and modifications.

What is claimed is:

1. An electrocadiograph system comprising:
a portable electrocardiograph for measuring and storing an electrocardiograph waveform;
a recorder having electric power and positioning means for reading said electrocardiograph waveform stored in said portable electrocardiograph;
signal transfer means for transferring electrical signals between said portable electrocardiograph and said recorder, said signal transfer means including a first electro-magnetic coupling having first coils for said portable electrocardiograph and said recorder; and
power transfer means including a second electro-magnetic coupling having second coils for said portable electrocardiograph and said recorder, said power transfer means transferring electric power from said recorder to said portable electrocadiograph, said power and positioning means positioning first and second coils of said portable electrocardiograph so that each coil of said portable electrocardiograph faces a corresponding coil of said recorder.

2. An electrocardiograph system according to claim 1, wherein said electrical signals include clock and data signals, said first electro-magnetic coupling of said electrocardiograph system further including an electro-magnetic coupling having independent coils to separately transfer said clock and data signals, wherein said data signal is transmitted and received by a single coil.

3. An electrocardiograph system comprising:
an electrocardiograph for measuring and storing an electrocardiograph waveform of a subject;
a recorder for reading and outputting said electrocadiographic waveform stored in said electrocardiograph;
transfer means for separately transferring electric power and electrical signals between said electrocardiograph and said recorder, said transfer means including first and second independent electro-magnetic couplings; and
noise removing means for removing at least electric power noise from said electrical signals, said noise removing means further comprising means for detecting a noise and means for adding the detected noise to the electrical signals with opposite phase so that the detected noise offsets the noise in the electric signals.

4. An electrocardiograph system according to claim 3, wherein said electrical signals include clock and data signals, said first electro-magnetic coupling of said electrocardiograph system further including independent electro-magnetic couplings to separately transfer said clock and data signals, said noise removing means removing noise of an electric power signal and clock signal from said data signal.

5. An electrocardiograph system comprising:
an electrocardiograph for measuring and storing an electrocardiograph waveform of a subject;
a recorder for reading and outputting said electrocardiograph waveform stored in said electrocardiograph;
transfer means having independent electro-magnetic couplings for separately transferring electric power and electrical signals between said electrocardiograph and said recorder; and
noise removing means for removing at least electric power noise from said electrical signals, said noise removing means including metal which is arranged to surround at least a portion of said transfer means to reduce a mixture of leakage magnetism into the electric signals transferred by said transfer means.

6. An electrocardiograph system according to claim 5, wherein said electrical signals include clock and data signals, said electro-magnetic coupling for transferring electrical signals of said electrocardiograph system further including independent electro-magnetic couplings to separately transfer said clock and data signals, the metal of said noise removing means surrounding at least a portion of the transfer means for transferring the data signals and removing noise due to electric power and a clock signal from the data signals.

7. An electrocardiograph system comprising:
an electrocardiograph for measuring an electrocardiograph waveform;
a recorder having positioning means for reading and outputting said electrocardiograph waveform stored in said electrocardiograph;
clock transfer means for transferring a clock signal in one direction between said electrocardiograph and said recorder, said clock transfer means including a first electro-magnetic coupling having a first independent coil; and
data transfer means for transferring data signals bidirectionally between said electrocardiograph and said record, said data transfer means including a second electro-magnetic coupling having another independent coil; and
positioning means for positioning coils of said portable electrocardiograph so that each coil of said portable electrocardiograph faces a corresponding coil of said recorder.

* * * * *

UNITED STATES PATENT AND TRADEMARK OFFICE
CERTIFICATE OF CORRECTION

PATENT NO. : 5,284,151
DATED : February 8, 1994
INVENTOR(S) : Masahiro Onoda

It is certified that error appears in the above-indentified patent and that said Letters Patent is hereby corrected as shown below:

In Column 1, line 51, delete "4,720,636" and insert -- 4,720,626 --.

In Column 6, line 63, delete "clock→clock coil driver→clock transfer coil" and insert -- clock→clock coil driver→clock transfer coil --.

In Column 7, lines 1-2, delete "data→data coil driver→data transmit/receive switching circuit (transmit)→data transfer coil" and insert -- data→data coil driver→data transmit/receive switching circuit (transmit)→data transfer coil --.

In Column 7, lines 8-9, delete "received data←data receiver←data transmit/receive switching circuit (receive)←data transfer coil" and insert -- received data←data receiver←data transmit/receive switching circuit (receive)←data transfer coil --.

In Column 7, line 14, delete "power coil driver→power coil" and insert -- power coil driver→power coil --.

UNITED STATES PATENT AND TRADEMARK OFFICE
CERTIFICATE OF CORRECTION

PATENT NO. : 5,284,151
DATED : February 8, 1994
INVENTOR(S) : MASAHIRO ONODA

It is certified that error appears in the above-indentified patent and that said Letters Patent is hereby corrected as shown below:

In Column 7, line 68, delete "electrocardiograph waveform" and insert -- electrocardiographic waveform --.

In Column 8, line 25, delete "electrocardiograph waveform" and insert -- electrocardiographic waveform --.

In Column 8, lines 26-27, delete "electrocardiograph waveform" and insert -- electrocardiographic waveform --.

In Column 8, lines 49-50, delete "electrocardiograph waveform" and insert -- electrocardiographic waveform --.

In Column 8, line 52, delete "electrocardiograph waveform" and insert -- electrocardiographic waveform --.

In Column 8, line 61, delete "record" and insert -- recorder --.

Signed and Sealed this

Fourteenth Day of June, 1994

Attest:

BRUCE LEHMAN

*Attesting Officer*    *Commissioner of Patents and Trademarks*